United States Patent
Awakowicz et al.

(10) Patent No.: US 7,229,590 B2
(45) Date of Patent: *Jun. 12, 2007

(54) STERILIZATION CHAMBER FOR STERILIZING OBJECTS

(75) Inventors: Peter Awakowicz, Munich (DE); Robert Frost, Landshut (DE); Gernot Keil, Munich (DE); Peter Georg Scheubert, Grosshelfendorf (DE)

(73) Assignee: Ruediger Haaga GmbH, Altoberndorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/759,071

(22) Filed: Jan. 20, 2004

(65) Prior Publication Data

US 2004/0146427 A1    Jul. 29, 2004

(30) Foreign Application Priority Data

Jan. 17, 2003   (DE)   ................................. 103 02 344

(51) Int. Cl.
*A61L 2/00*   (2006.01)

(52) U.S. Cl. .................. 422/28; 422/1; 422/3; 422/26; 422/27

(58) Field of Classification Search ............ 422/1, 422/3, 26, 27, 28, 33, 292, 293, 295, 297, 422/298
See application file for complete search history.

(56) References Cited

U.S. PATENT DOCUMENTS

| 4,512,951 | A | * | 4/1985 | Koubek | 422/33 |
| 4,704,254 | A | * | 11/1987 | Nichols | 422/28 |
| 4,952,370 | A | * | 8/1990 | Cummings et al. | 422/28 |
| 5,173,259 | A | * | 12/1992 | Bordini | 422/28 |
| 5,525,295 | A | * | 6/1996 | Pflug et al. | 422/27 |
| 6,572,819 | B1 | * | 6/2003 | Wu et al. | 422/28 |

FOREIGN PATENT DOCUMENTS

DE   101 16 395 A1   3/2001

\* cited by examiner

*Primary Examiner*—Krisanne Jastrzab
(74) *Attorney, Agent, or Firm*—Crowell & Moring LLP

(57) ABSTRACT

Described is a sterilization chamber for sterilizing objects for application in a process in which a vapour composite, composed of water vapour and hydrogen peroxide vapour, is guided without a carrier gas flow into the sterilization chamber in which a vacuum prevails, whereby the vapour composite settles on the surfaces of the objects to be sterilized and on the surfaces of the sterilization chamber in the form of a condensation layer, which is suctioned off by means of further evacuation of the sterilization chamber after a certain reaction time. In accordance with the present invention, the surfaces of the sterilization chamber consist of poor heat-conducting, water-repellent material.

8 Claims, 1 Drawing Sheet

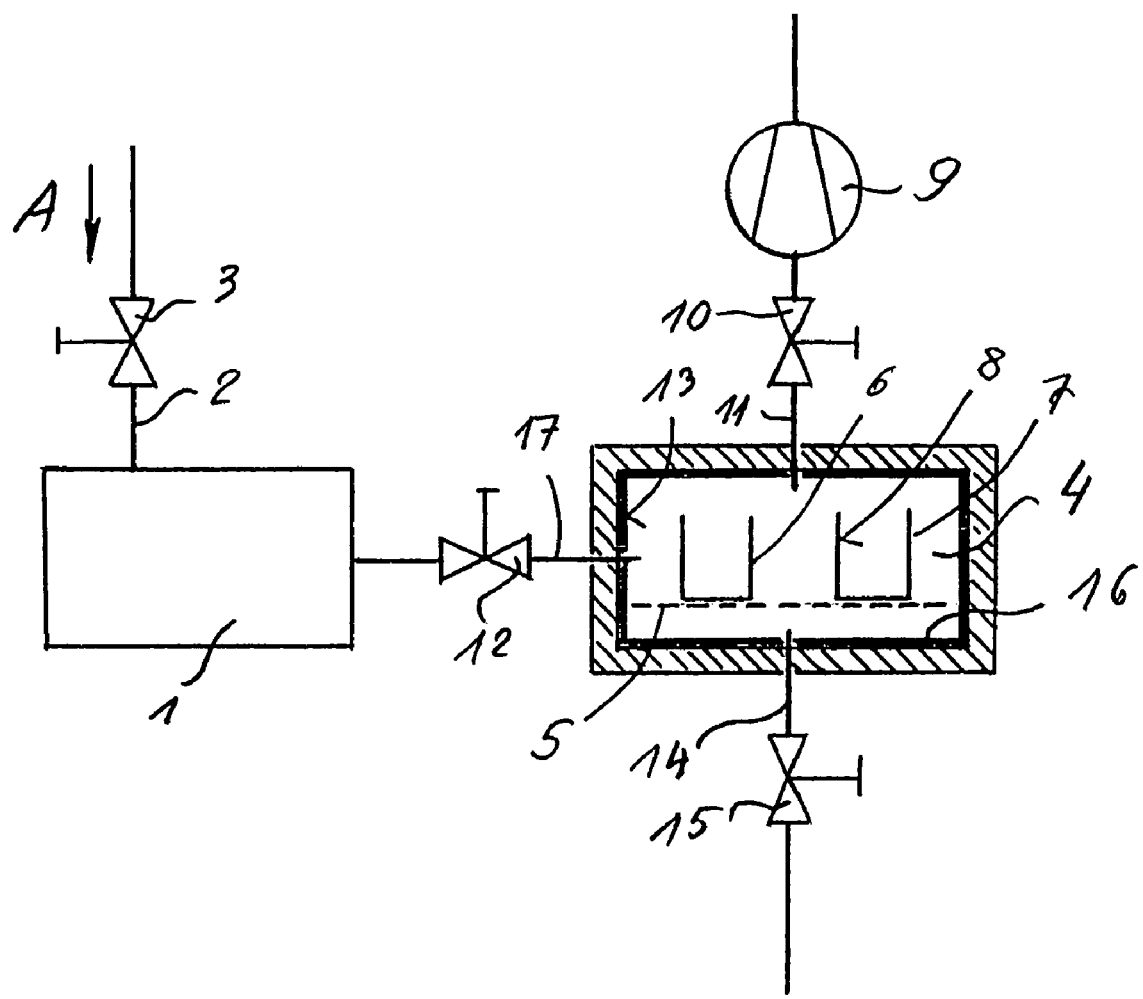

STERILIZATION CHAMBER FOR STERILIZING OBJECTS

CROSS-REFERENCE TO RELATED APPLICATION

This application claims the priority of Application No. 13 02 344.5, filed Jan. 17, 2003, the disclosure of which is expressly incorporated by reference herein.

BACKGROUND AND SUMMARY OF THE INVENTION

The present invention relates to a sterilization chamber for sterilizing objects, comprising a vacuum conduit connected to a vacuum pump, also comprising a conduit for a vapor composite consisting of water vapor and hydrogen peroxide vapor, and comprising a conduit for flood gas for application in a process in which the vapor composite, fed without carrier gas flow into the sterilization chamber in which a vacuum prevails, settles on the surfaces of the objects to be sterilized and on the surfaces of the sterilization chamber in the form of a condensation layer, which is suctioned off after a pre-determined reaction time by means of further evacuation of the sterilization chamber.

A sterilization chamber of this kind is prior art in German published patent application 101 16 395. In the process which is carried out in the known sterilization chamber, the sterilizing effect occurs at the moment of condensation. This moment in time can be understood to be the time needed for the condensation out of the gas phase. Depending on the technical embodiment, this could be a matter of several tenths of a second, in particular in the case of sudden, adiabatic expansion, or a matter of seconds in the case of other embodiments of the evaporator required for the purpose. The sterilization effect is understood to be caused by the released evaporation enthalpy which occurs during condensation. The evaporation enthalpy delivers the necessary energy in order to dissociate a hydrogen peroxide molecule to such an extent that an oxygen atom is released. It is supposed that this chemical, highly reactive atomic oxygen is responsible for the killing of microorganisms.

In a sterilization chamber intended for this process, on which the present invention is based, there exist in practice certain problems. These arise from the fact that such sterilization chambers have metal surfaces, which can result in a series of disadvantages. In connection with this, some basic theoretical factors are premised.

The vapor composite used comprises water and hydrogen peroxide molecules. Both molecules have electric dipoles, which, in the near field, that is in distances in the order of magnitude of molecular dimensions, have a spatially inhomogenous distribution of the electric charge. When the vapor composite flows into the sterilization chamber, the dipoles do not only reach the surfaces of the objects to be sterilized, but also the metal surfaces of the sterilization chamber. The three-dimensional material structure of the solid state is disturbed, however, on the surfaces. Due to released bonding arms of the atoms deposited on the surface, as well as the plurality of atoms from alloyed components and material impurities, which also lie on the surface, local electric charge centers arise, which are positive at some places and negative at others. Electrical dipoles can adhere to these electric surface charges as they skim over the surfaces and must aligned themselves spatially according to the prevailing charge distribution on the metal surfaces. This process of the bonding of atoms or molecules on the surfaces by means of electric interaction is called adsorption. In the present case, water and hydrogen peroxide molecules from a vapor phase are involved here, which are very strong dipoles and adsorb very quickly and fixedly on metal surfaces.

It is understood that, by bringing the vapor composite into the sterilization chamber, which comprises metal surfaces, a greatly inhomogenous macroscopic layer of fluid first forms on the metal surface. This results, in a very short time, in macroscopic drops of condensation. A large percentage of the evaporation enthalpy which occurs during the condensation process is hereby not used to heat the condensate, but rather—due to the good heat-conducting qualities of the metal surface—is removed quickly from the condensate layer. If there are objects to be sterilized in the sterilization chamber, in particular made from poor heat-conducting material, for example, PET bottles, which heat up quickly on their surface due to the layer of condensation, the fed vapor composite will preferably condense on the colder surfaces, that is, on the metal surfaces of the sterilization chamber. This means that not enough vapor volume and thus not enough condensation mass remains for the objects which are to be sterilized.

Metal surfaces of sterilization chambers therefore have the following disadvantages:

Firstly, drops cannot evaporate quick enough on the very wide surface areas of larger diameters and thus cannot be suctioned off quick enough after sterilization has taken place. This results in the metal surfaces becoming very wet locally. Secondly, too much vapor condenses unnecessarily on the metal surfaces, which requires basically an unnecessarily powerful vapor supply and in addition an unnecessarily strong suction action. Thirdly, the metal surfaces actually pump off the vapor mass required elsewhere. The metal surfaces act like vacuum pumps, which pump out the particles from the volume in such a way that they at first condense them and finally bind the fluid phase by means of removing the condensation heat. In the case of the known sterilization chamber, an excessive amount of vapor has to be fed in, of which the greatest percentage condenses on the surfaces of the sterilization chamber and on all remaining metal parts, while for the objects to be sterilized, in particular those made of poor heat-conducting material, not enough condensation remains to ensure a complete sterilization process.

It is an object of the present invention to avoid the above mentioned disadvantages and in particular to improve the sterilization effect on the objects to be sterilized.

This object has been achieved in accordance with the present invention in that the surfaces of the sterilization chamber are made of poor heat-conducting, water-repellent material.

Surfaces of this type do not conduct the heat away immediately which occurs during condensation so that the heat can be used to heat the condensation and to activate the hydrogen peroxide. In addition, the number of electrical surface charges is significantly reduced, so that excess condensation on the surfaces of the sterilization chamber is prevented to a reasonable degree.

Insofar as it is possible from the point of view of design, those component parts of the sterilization chamber which come into contact with the condensation layer can be advantageously manufactured from plastic, glass or any suitable closed-pore ceramic material. Alternatively, in particular when required due to reasons of stability, metal sterilization chambers can be used, whose surfaces have a layer of plastic, glass or closed-pore ceramic material. The surfaces of such sterilization chambers according to the present invention should be smooth and free of tool marks, so that no surface roughness acts itself as a condensation starting point and thus reduce the desired effect. Many different plastics can be considered for the poor heat-conducting, water-repellent surface, for example, Acrylat, PP, PU, PVC, PE, PTFE, PFA and others.

All these plastics could form a coating covering the surface of the sterilization chamber so that not too many surfaces charges would be found. The coating thickness can vary from a few micrometers to a few millimeters, depending on the material. Those plastics which are not corroded by hydrogen peroxide vapor are particularly suitable for application. The coating material should not be porous, as the pores would become soaked and could not be sufficiently dried out again.

Particularly suitable are plastics on a PTFE base with a very strong water-repelling surface, which have a water take-up of practically zero and a high temperature capacity of over 200° C. It should be remembered that the surfaces are continuously covered and recovered by the condensation layer, which is greatly heated during condensation from the vapor phase by means of the released evaporation heat. Momentary condensation temperatures of between 100° to 150° C. are possible, depending on application. Moreover, the vapor composite has in the moment it flows into the sterilization chamber a temperature of up to 140° C. The surfaces of the sterilization chamber must be able to withstand this level of heat.

It has been shown that even plastics which catalytically decompound the hydrogen peroxide, for example, silicon, can be used. Tests have shown that such materials, which are normally unsuited to an application with hydrogen peroxide because they catalytically decompound it, are by all means suited for the coating of metal surfaces in sterilization chambers. An example of such a material in this case would be silicon rubber. The condensation layer formed sterilizes such surfaces before the hydrogen peroxide decomposes thereon, as in the named process the sterilization effect occurs in the moment of condensation out of the vapor phase.

These and further objects, features and advantages of the present invention will become more readily apparent from the following detailed description thereof when taken in conjunction with the accompanying schematic drawing.

BRIEF DESCRIPTION OF THE DRAWING

In the case of the shown installation a vapor composite of water vapor and hydrogen peroxide vapor is generated. A watery solution containing hydrogen peroxide to the desired concentration is fed via a conduit 2 and a valve 3 under pressure in direction A to an evaporator 1.

DETAILED DESCRIPTION OF THE DRAWING

A sterilization chamber 4 is arranged downstream of the evaporator 1, in which sterilization chamber 4 objects 6,7 whose surfaces 8 are to be sterilized are located, placed on a suitable support 5. PET bottles can be involved in this case.

Firstly, the sterilization chamber 4 is evacuated by means of an suitable vacuum pump 9. The sterilization chamber 4 is subsequently isolated from the vacuum pump 9 by closing a valve 10, so that there is no longer a suction action generated via the vacuum conduit 11.

By opening a valve 12 it is ensured that the vapor composite located in the evaporator 1 reaches the sterilization chamber 4 via a conduit 17, preferably by means of adiabatic expansion. The pressure in the evaporator 1 must, as a consequence, be significantly higher than the pressure in the sterilization chamber 4. During expansion, the volume taken up by the vapor composite increases, whereby the vapor composite cools down to below dew point and thus suddenly condenses on all accessible surfaces 8 of the objects 6 and 7 as well as the support 5 and the surfaces 13 of the sterilization chamber 4. The pressure in the sterilization chamber 4 hereby increases again. With the aid of the vacuum pump 9, the condensation layer is drawn off within seconds, and the sterilization chamber 4 is ventilated with a flood gas via a conduit 14 and a valve 15.

In a process of this type, the vapor composite, fed in without a carrier gas flow, settles in the form of a sudden condensation layer on the surfaces 8 of the objects 6 and 7 to be sterilized as well as on the surfaces 13 of the sterilization chamber 4, whereby the condensation layer is suctioned off out of the sterilization chamber 4 after a short reaction time by means of further evacuation, namely at a pressure of below 10 mb, preferably at approximately 1 mb.

If the surfaces 13 of the sterilization chamber 4 are made of metal, as is the case in prior art, the above described problems and disadvantages occur. It is, in accordance with the present invention, therefore provided that the surfaces 13 of the sterilization chamber 4 consist of poor heat-conducting, water-repellent material, while having for example a coating 16 of plastic, glass or closed-pore ceramic material. This prevents the condensation layer from settling primarily on the surfaces 13 of the sterilization chamber 4 and not sufficiently on the surfaces 8 of the objects 6 and 7 to be sterilized. By applying the features of the present invention, an increase in the sterilizing effect is achieved on the one hand, while on the other the duration of the sterilization process is shortened, whereby in addition the process of suctioning off the generated condensation layer is improved.

The invention claimed is:

1. A method of sterilizing an object, said method comprising the step of:
   exposing an object to a vapor composite which is rapidly expanded within a sterilizing chamber wherein expanding and condensing the vapor composite takes place within several tenths of a second such that the vapor composite cools to below the hydrogen peroxide dew point and condenses on all accessible surfaces of the object, said sterilizing chamber having component parts which come into contact with a condensation layer, said component parts being configured from a material selected from the group consisting of plastic, glass or a closed-pore ceramic material.

2. The method of claim 1, further comprising the steps of:
   evacuating the sterilization chamber using a vacuum pump;
   providing the vapor composite to the sterilization chamber to form the condensation layer;
   removing the condensation layer; and
   ventilating the sterilization chamber.

3. The method of claim 2, wherein said step of evacuating the sterilization chamber further comprises the step of isolating the sterilization chamber from the vacuum pump with a valve.

4. The method of claim 1, wherein said vapor composite comprises water and hydrogen peroxide.

5. The method of claim 2, wherein said step of removing the condensation layer further comprises evacuating the sterilization chamber.

6. The method of claim 5, wherein said step of evacuating the sterilization chamber is conducted at a pressure of from 10 mb to 1 mb.

7. The method of claim 5, wherein said step of evacuating the sterilization chamber is conducted at a pressure of approximately 1 mb.

8. The method of claim 1, wherein said step of removing the condensation layer is performed after a predetermined reaction time.

* * * * *